United States Patent [19]

Wallace et al.

[11] Patent Number: 5,046,669

[45] Date of Patent: * Sep. 10, 1991

[54] SYRINGE DISPOSAL APPARATUS AND METHOD

[75] Inventors: Arthur W. Wallace, Aurora; Jack R. Sorwick, Parker; Thomas Pearce; Philip E. Clements, both of Littleton; David E. Wood, Englewood, all of Colo.

[73] Assignee: National Syringe Disposal, Inc., Englewood, Colo.

[*] Notice: The portion of the term of this patent subsequent to Mar. 6, 2007 has been disclaimed.

[21] Appl. No.: 485,594

[22] Filed: Feb. 27, 1990

Related U.S. Application Data

[63] Continuation-in-part of Ser. No. 316,465, Feb. 27, 1989, Pat. No. 4,905,916.

[51] Int. Cl.⁵ .................................... B02C 19/14
[52] U.S. Cl. ........................... 241/23; 241/63; 241/65; 241/99; 241/DIG. 38
[58] Field of Search ............... 241/99, 190, 69, 73, 241/152 A, 154, 65, 23, 24, 29, DIG. 38, 36, 34, 63

[56] References Cited

U.S. PATENT DOCUMENTS

| | | | |
|---|---|---|---|
| 3,929,295 | 12/1975 | Montalbano | 241/190 |
| 3,958,765 | 5/1976 | Musselman | 241/99 |
| 4,205,794 | 6/1980 | Horton et al. | 241/99 X |
| 4,905,916 | 3/1990 | Sorwick et al. | 241/99 X |

Primary Examiner—Mark Rosenbaum
Attorney, Agent, or Firm—W. Scott Carson

[57] ABSTRACT

A syringe disposal apparatus has a portable collection unit (1) and a processing unit (2'). The collection unit (1) has an in-feed mechanism (11) to allow syringes to be introduced into the collection unit (1); and an interlock mechanism (12) suitable for removably securing the collection unit (1) to the processing unit (2') and emptying the syringes from the collection unit (1) into the processing unit (2'). The processing unit (2') contains an interlock mechanism (20) suitable to activating the collection unit interlock mechanism (11); a hammer mill (43) for initially breaking up the syringes (45) into discrete pieces (45'); a paddle wheel (44) to regulate the passage of the broken syringe pieces to a grinder (21) suitable for grinding the syringes into particles of metal and plastic; a crucible assembly (22) suitable for heating these particles above the melting point of plastic, and then cooling to produce a solid puck of plastic in which the metal particles are suspended and encapsulated; and a controlling means (50) to coordinate the efficient operation of the members of the processing unit (2').

24 Claims, 17 Drawing Sheets

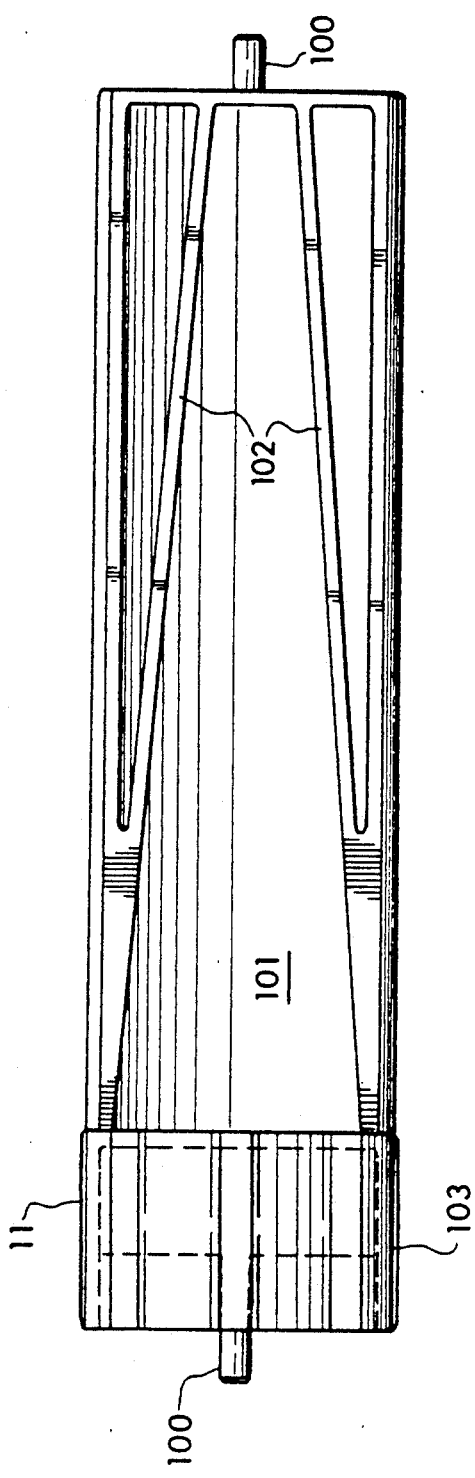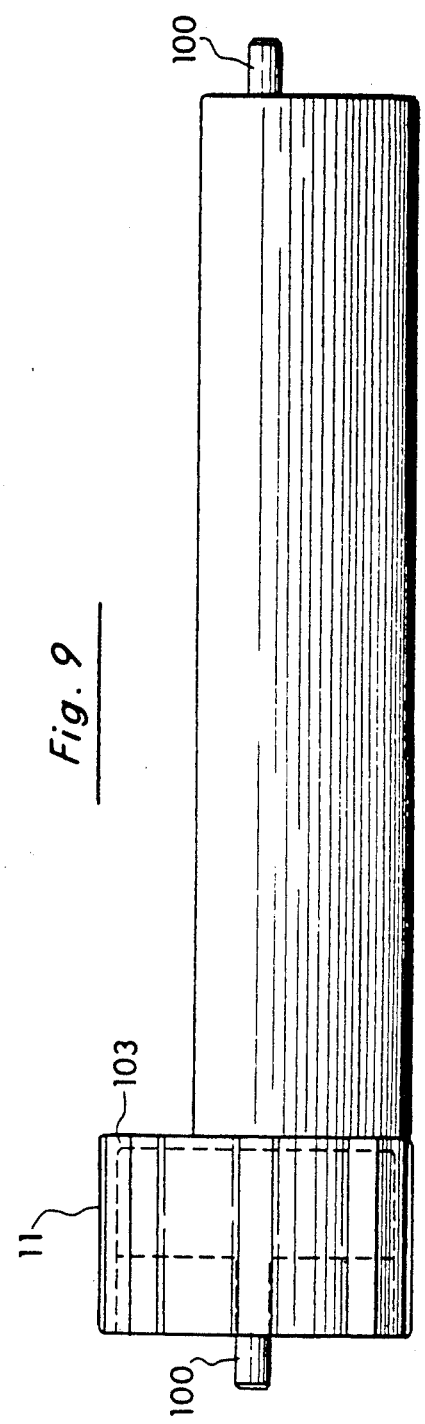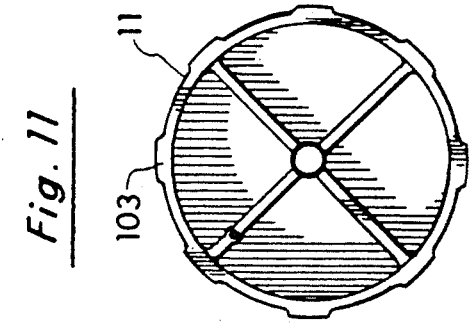

Fig. 13
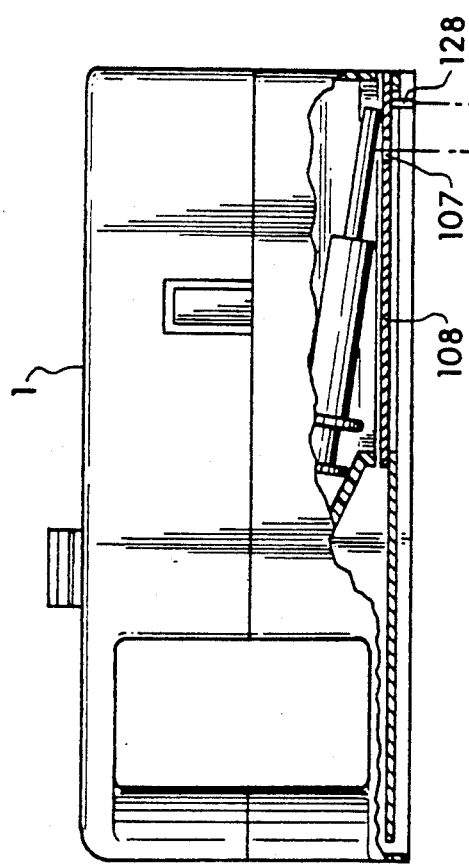
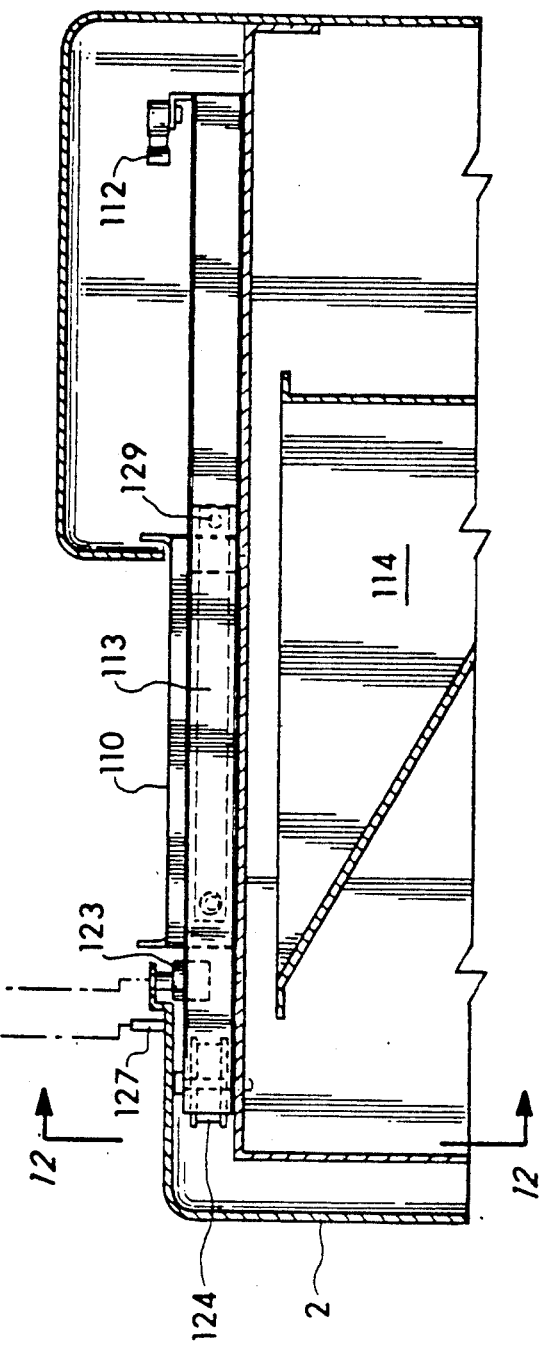

SYRINGE DISPOSAL APPARATUS AND METHOD

RELATED APPLICATIONS

This application is a continuation-in-part of U.S. patent application Ser. No. 316,465 filed Feb. 27, 1989, now U.S. Pat. No. 4,905,916.

BACKGROUND OF THE INVENTION

1. Field of the Invention

The present invention relates generally to the field of devices employed to dispose of used syringes, and in particular to devices used to collect and then grind up and melt used syringes.

2. Statement of the Problem

Hypodermic syringes are widely used in hospitals and other medical facilities for a variety of purposes, including, for example, drawing of blood and other patient fluid samples, and for administration of medication. Such hypodermic syringes are commonly provided as individually prepackaged, sterilized, disposable items intended for use a single time after which they are discarded, thereby avoiding relatively costly and time-consuming re-sterilization. However, disposal of used syringes must be accomplished in a manner that safely avoids injury to medical personnel, such as inadvertent needle punctures and potentially contaminating contact with the used syringe. In particular, it is imperative to minimize exposure of medical personnel to dangerous organisms such as HIV and hepatitis viruses that may be present in used syringes. It is also highly desirable to dispose of used syringes in a manner that minimizes the opportunity or risk of unauthorized reuse, for example, by drug abusers. Finally, improper disposal of medical waste poses a danger to the general public.

3. Solution to the Problem

None of the prior art employs a two-part syringe disposal apparatus having a processing unit and a separate portable collection unit that can be easily carried from room to room in a health care facility to collect used syringes. A single processing unit at a central location is then used to process the used syringes gathered by the collection units. The collection unit has an infeed mechanism to allow used syringes to be individually fed into the unit, and an interlock mechanism adapted to removably secure the collection unit to the processing unit for the purpose of emptying syringes from the collection unit without further exposure to medical personnel. After being emptied into the processing unit, the syringes are initially broken into discrete pieces and thereafter ground up, and the resulting particles of metal, plastic, and rubber are then heated beyond the melting point of the plastic to form a solid puck in which the metal particles are suspended and encapsulated. The heating process also sufficient to sterilize the particles and eliminate any microorganisms that were present.

SUMMARY OF THE INVENTION

This invention provides a syringe disposal apparatus having a separate portable collection unit and a processing unit. The collection unit has an infeed mechanism to allow syringes to be individually introduced into the collection unit; and an interlock mechanism suitable for removably securing the collection unit to the processing unit and emptying the syringes from the collection unit into the processing unit. The processing unit contains an interlock mechanism suitable to activating the collection unit interlock mechanism; a hammer mill for initially breaking up the syringes into discrete pieces; a paddle wheel to regulate the passage of the broken syringe pieces to a grinder suitable for grinding the syringes into particles of metal, plastic, and rubber; a crucible assembly suitable for heating these particles above the melting point of plastic, and then cooling to produce a solid puck of plastic in which the metal particles are suspended and encapsulated; and a controlling means to coordinate the efficient operation of the members of the processing unit.

A primary object of the present invention is to provide an apparatus for destruction and decontamination of used syringes that minimizes the risk of accidental injury or infection to medical personnel.

Another object of the present invention is provide a small portable in-room unit for collection of used syringes that is cost-effective and easy to use.

Yet another object of the present invention is to convert used syringes into a form (i.e. a solid plastic puck encapsulating the metal fragments from the needle) that can be safely discarded without risk to the general public.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 9 is a side view of the rotatable door used to introduce syringes into the collector unit.

FIG. 10 is a top view of the rotatable door corresponding to FIG. 9.

FIG. 11 is an end view of the rotatable door corresponding to FIG. 9.

FIG. 13 is a side cross-sectional view generally corresponding to FIG. 12 showing the interlock mechanisms of the collection unit and the processing unit prior to initial engagement of the units.

DETAILED DESCRIPTION OF THE PREFERRED EMBODIMENTS

Figure 2:
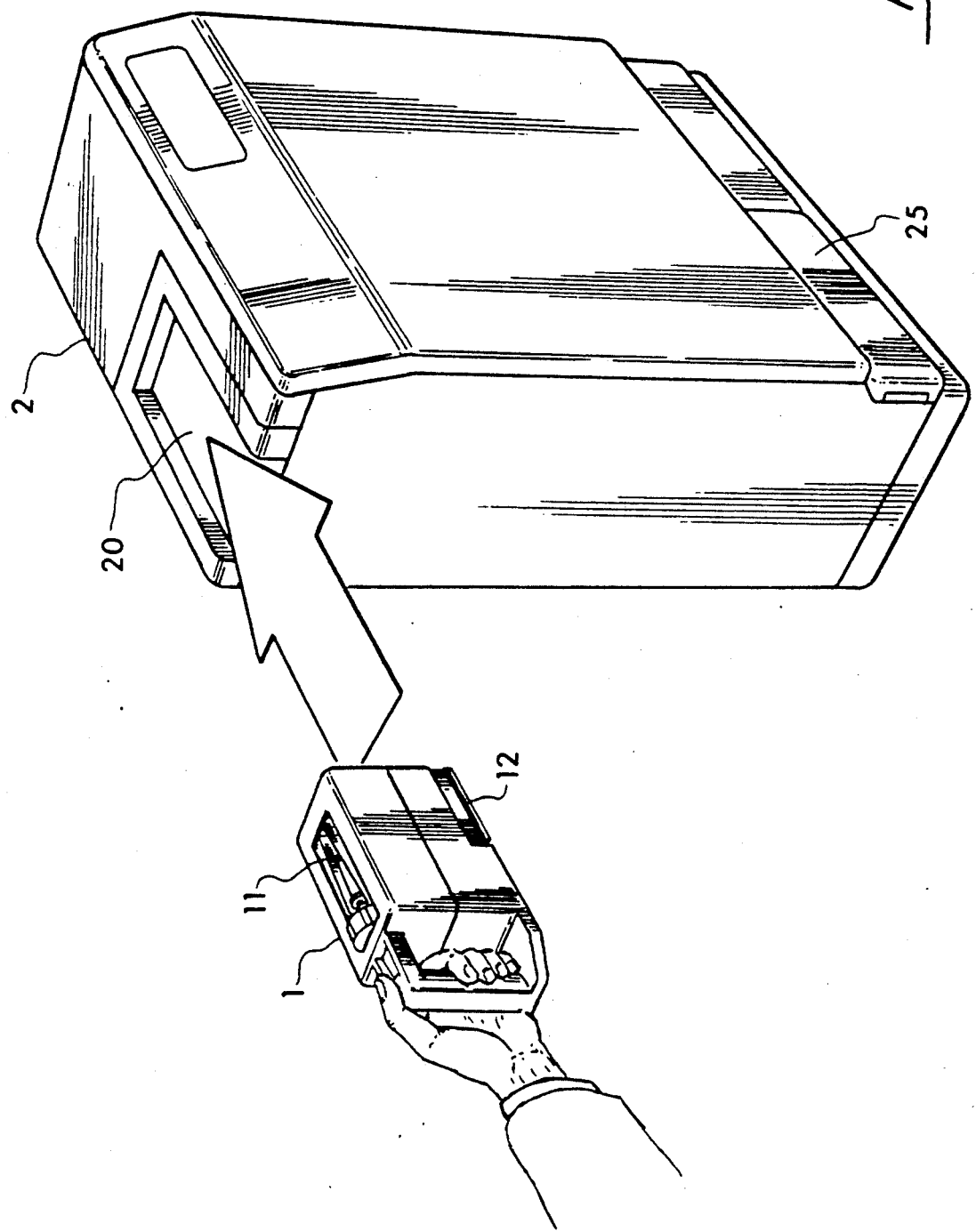
FIG. 2 is a perspective view showing the manner in which the collection unit is inserted into the processing unit.
Figure 6:
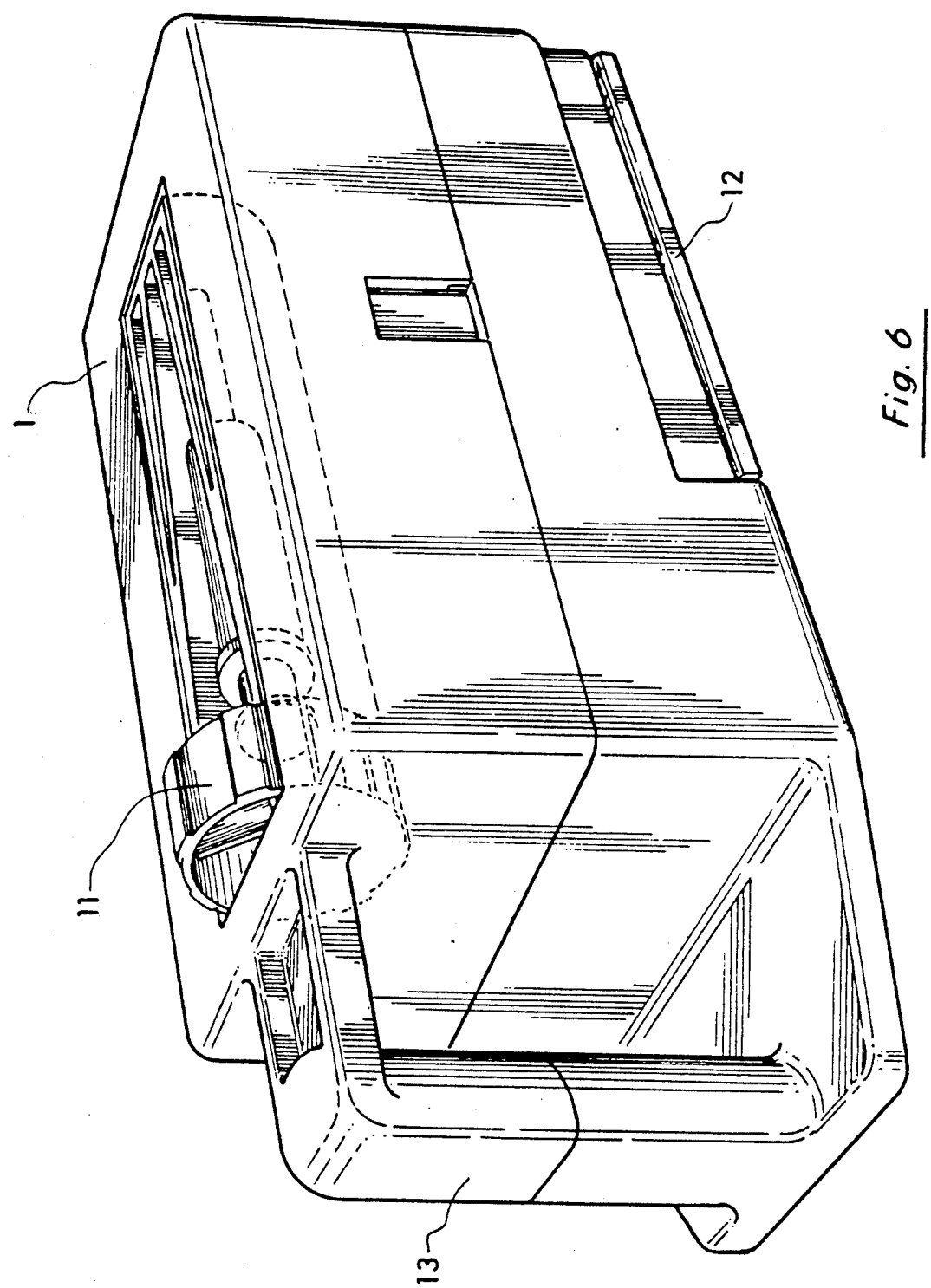
FIG. 6 is a perspective view of the collection unit.
Figure 7:
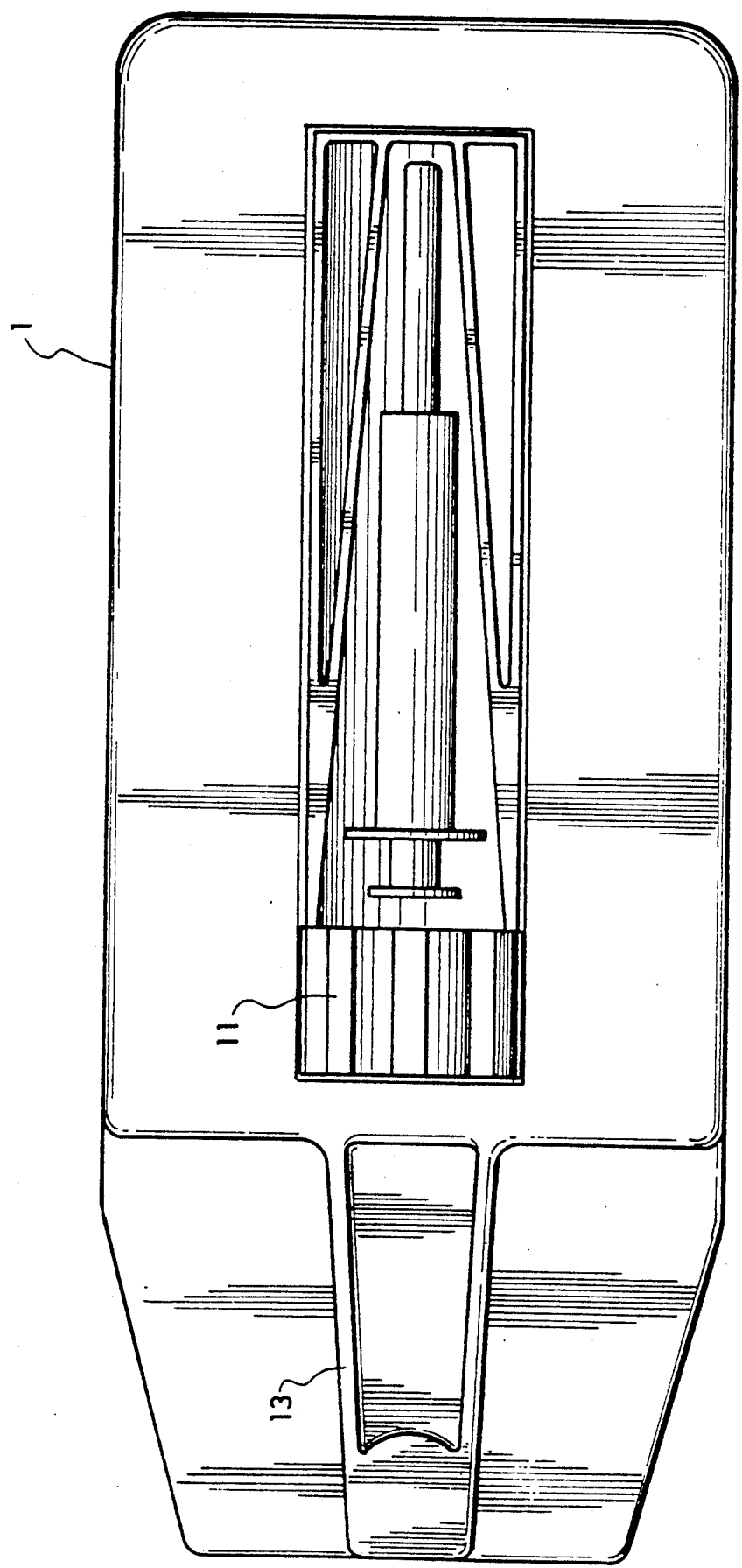
FIG. 7 is a top view of the collection unit.
Figure 8:
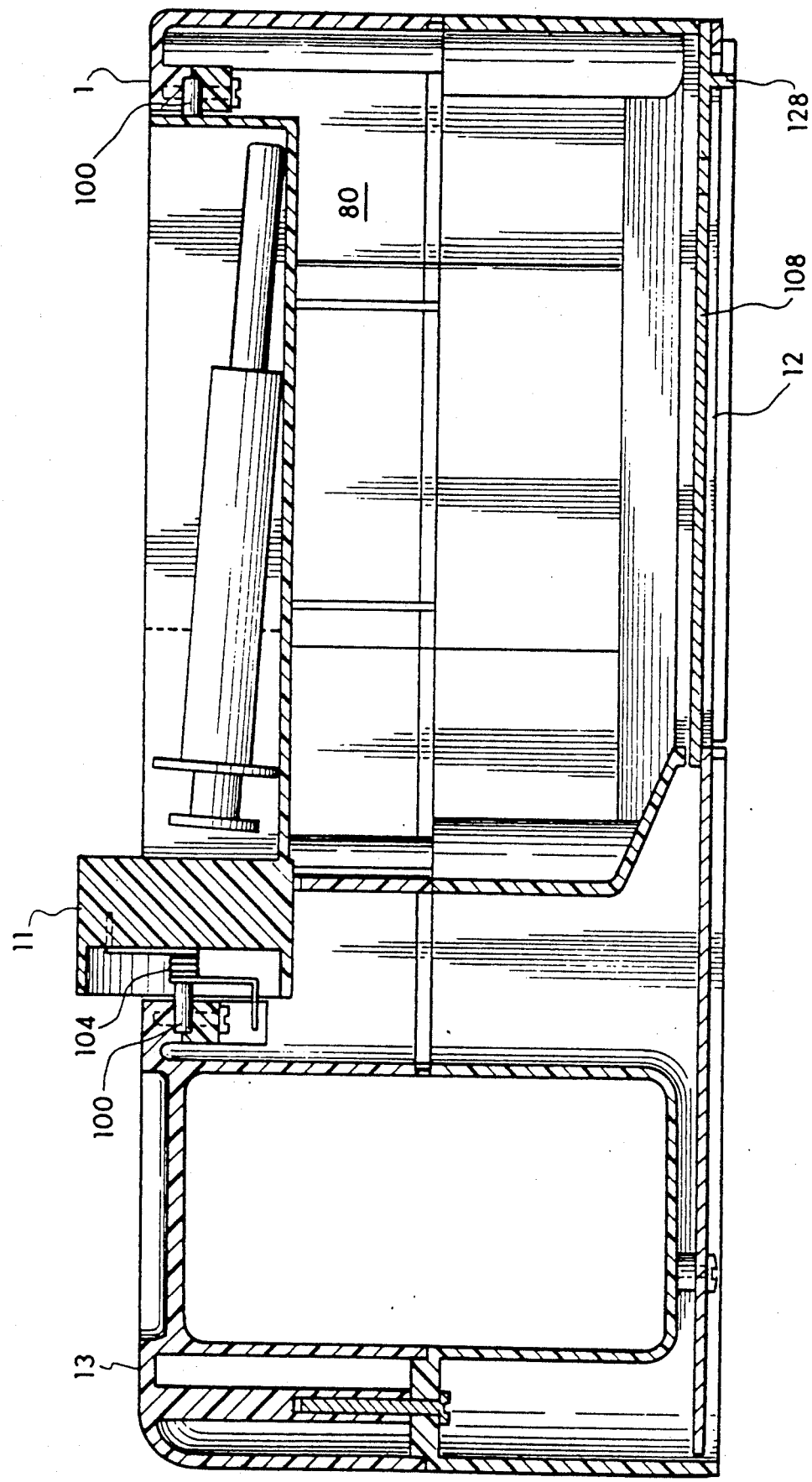
FIG. 8 is a vertical cross-sectional view of the collection unit.

Turning to FIG. 2, the collection unit 1 and processing unit 2, which comprise the apparatus, are shown in perspective view. As shown in greater detail in FIGS. 6 through 8, the collection unit 1 is a small, portable container that can be easily carried from room to room in a hospital to gather used syringes. One end of the collection unit 1 serves as a convenient handle 13 for carrying the unit. The top of the collection unit has an in-feed mechanism in the form of a rotatable door 11 that allows syringes to be individually fed into the internal chamber 80 of the unit. The in-feed mechanism is shown in greater detail in FIGS. 9 through 11. The rotatable door 11 has a generally cylindrical configuration, with a portion of the exterior of the cylinder cut away to form a receptacle 101 for receiving individual syringes. Two tapered guides 102 extend diagonally along a portion of the length of this receptacle 101 to create a trapezoidal cross-section for the receptacle, and thereby insure that syringes can only be placed into the receptacle with the needle of the syringe pointing away from the handle 13. The rotatable door 11 is rotatably secured over a corresponding opening in the top of the collection unit 1 by means of two hinge pins 100 that are seated in holes in the collection unit's casing. After a syringe has been placed in the receptacle 101, the rotatable door 11 is manually rotated by means of a thumb wheel 103 to an inverted position. The syringe falls by gravity from the receptacle 101 into the interior chamber 80 of the collection unit. The rotatable door 11 is then returned to its initial position by a return spring 104 to accept the next syringe. The length and cylindrical diameter of the rotatable door are only slightly smaller than the length and width of this opening. Thus, any syringes held in the collection unit can not easily reemerge through this opening, regardless of the position of the rotatable door.

The bottom of the collection unit has an interlock mechanism 12 which can be triggered to empty the syringes from the collection unit. The interlock mechanism is specifically designed to be tamper-resistant and to minimize the risk of accidental activation.

Figure 1:
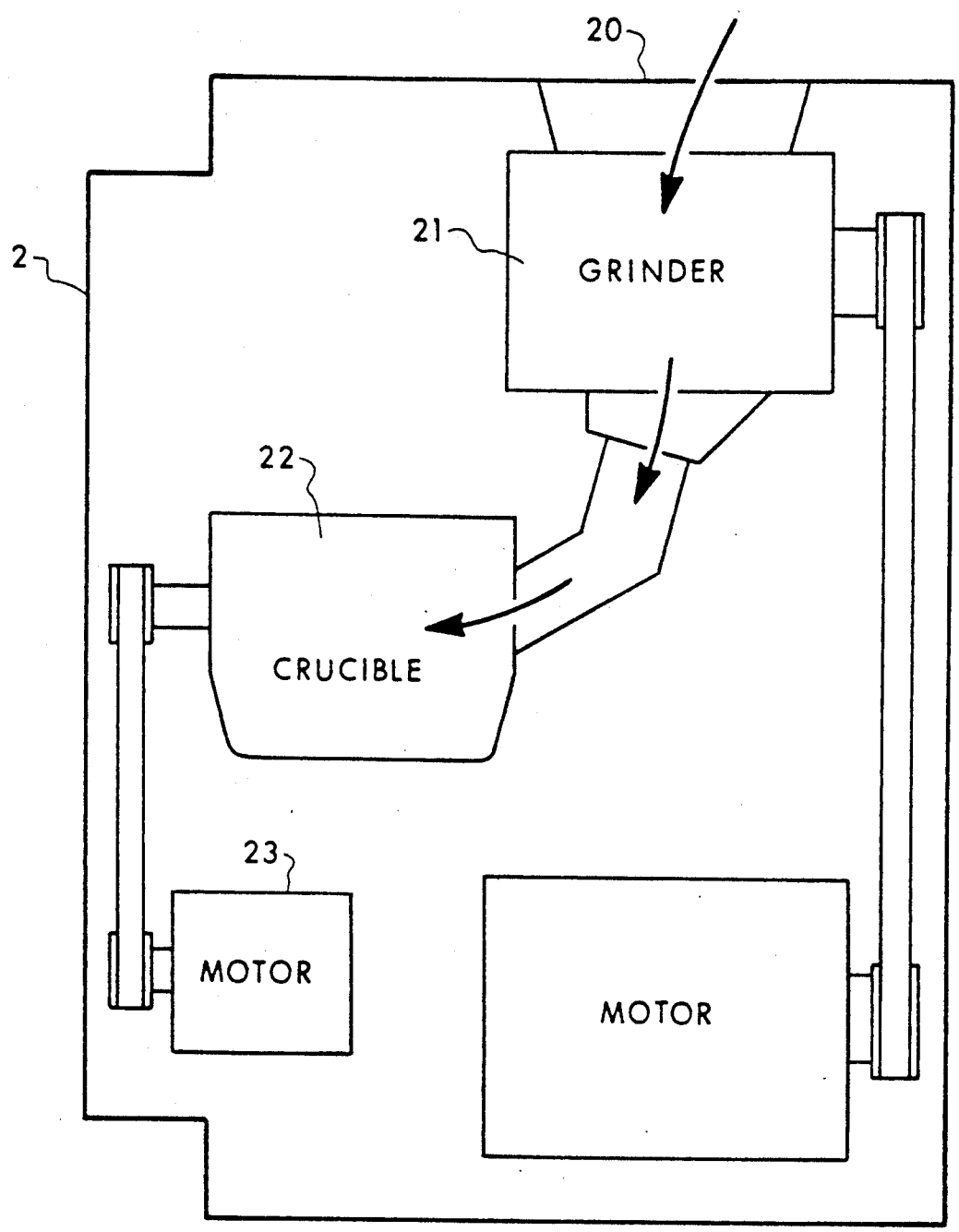
FIG. 1 is a simplified side view of the processing unit.

The processing unit 2 has a modular housing to protect its internal components. These components are shown in simplified schematic form in FIG. 1. A corresponding interlock mechanism 20 located on the top of the processing unit 2 interfaces with the interlock mechanism 12 on the collection unit 1 to unlock and open corresponding sliding doors on both units. These interlock mechanisms 12 and 20 are activated by sliding the collection unit 1 into place with respect to the processing unit 2, as shown in FIGS. 2, 3, 13 and 14. All of the used syringes contained in the interior chamber 80 are allowed to fall out of the collection unit and into the processing unit.

Figure 12:
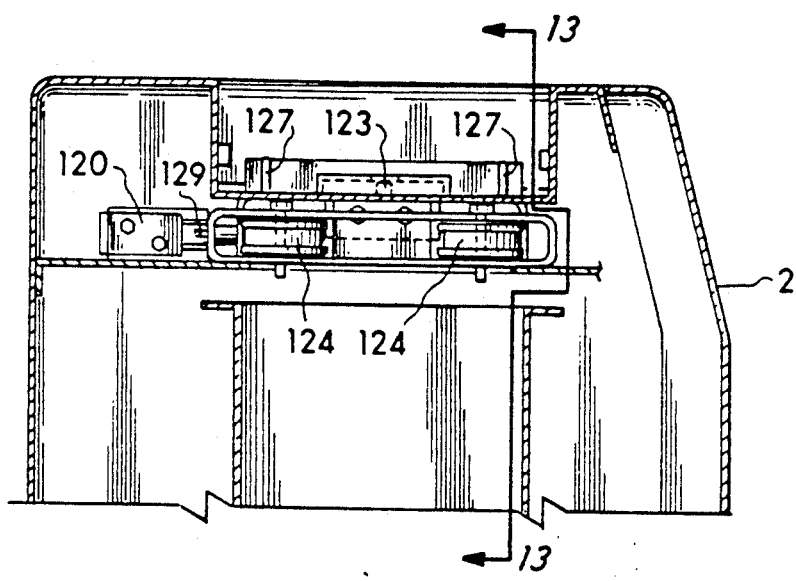
FIG. 12 is an end cross-sectional view showing the interlock mechanism at the upper left corner of the processing unit.
Figure 14:
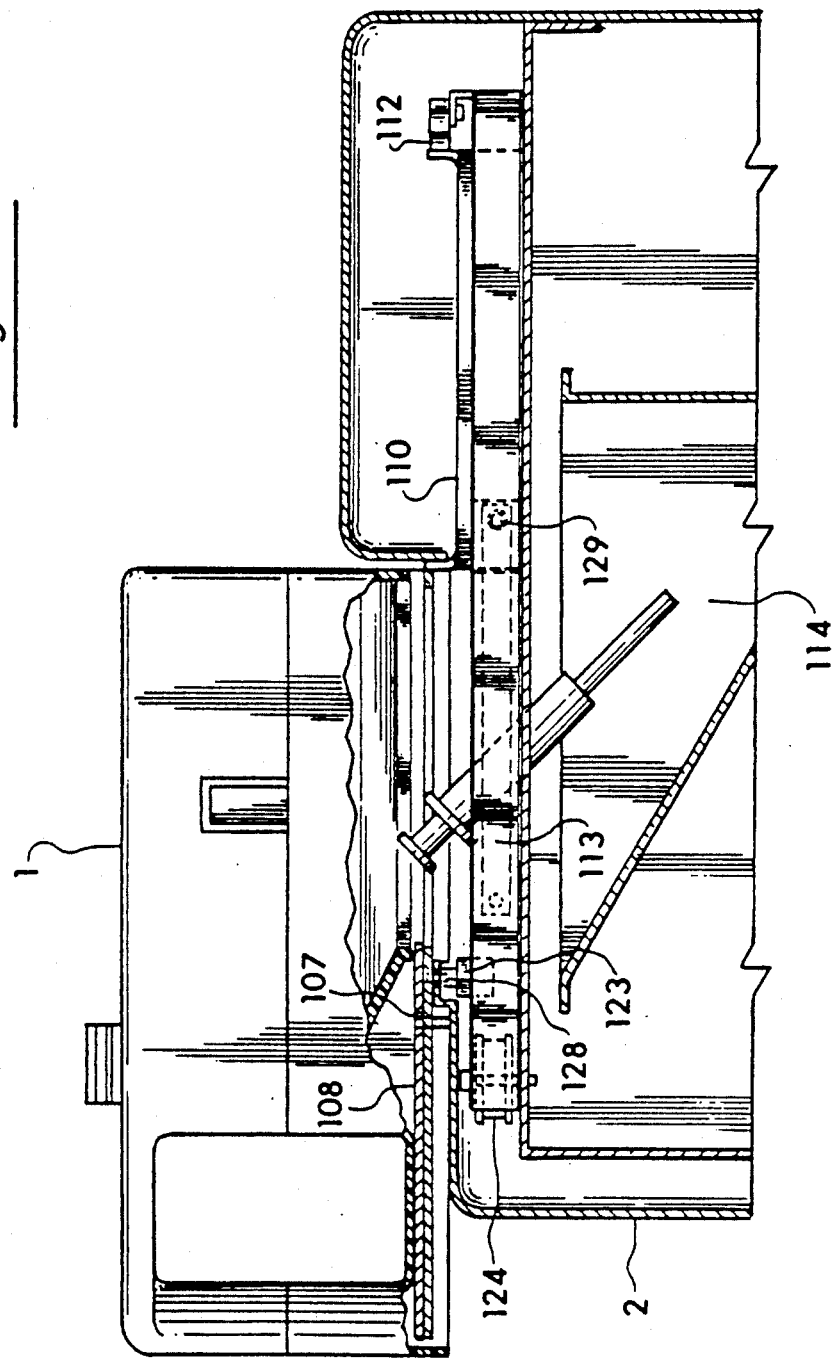
FIG. 14 is a side cross-sectional view generally corresponding to FIG. 13 showing the interlock mechanisms of the collection unit and the processing unit after engagement of the units.

The interlock mechanisms of the preferred embodiment of the present invention are shown in greater detail in FIGS. 12 through 14. After a sufficient quantity of syringes have been collected, the collection unit 1 is gradually lowered by the user onto the interlock mechanism 20 on the upper left corner of the processing unit. Longitudinal slots in the bottom surface of the collection unit guide the entry of two engagement pins 127 extending upward from the processing unit 2 into corresponding holes 107 in the sliding door 108 in the bottom of the collection unit 1. These pins 127 arrest motion of the collection unit door 108 relative to the processing unit 2, and simultaneously upwardly displace two latch springs located inside the collection unit to allow the door 108 to slide longitudinally with respect the bottom of the collection unit 1.

Figure 3:
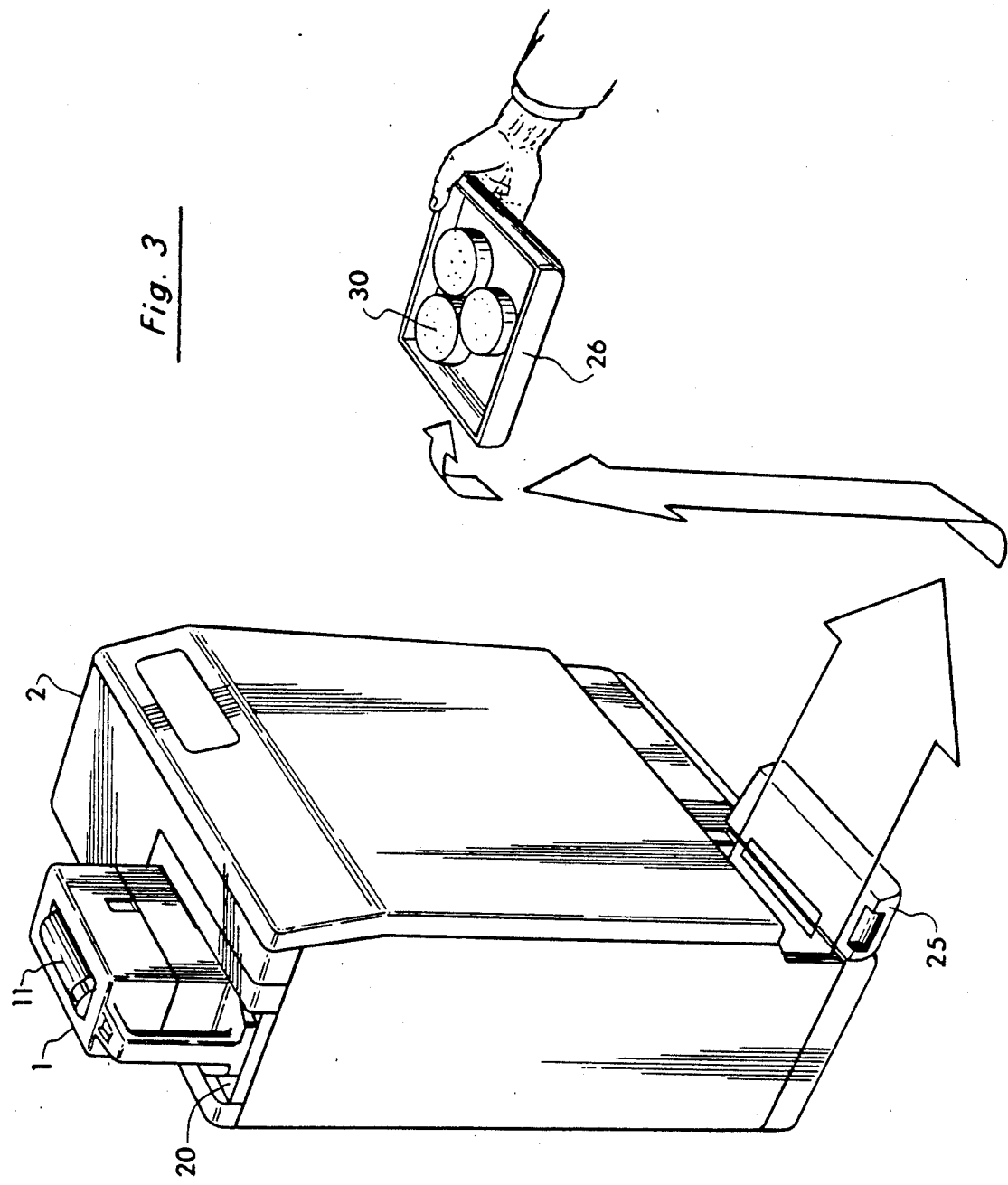
FIG. 3 is a perspective view showing the collection unit inserted into the processing unit, and also showing the manner in which a tray holding several processed pucks of melted plastic and metal particles resulting from the disposal process is removed through an access door in the bottom of the processing unit.

A second sliding door 110, located on the top of the processing unit 2, covers the in-feed chute to the grinder 21. This door 110 is generally locked in a shut position by a solenoid-activated locking pin 129. Simultaneous with the preceding engagement, a third engagement pin 128 extending downward from the collection unit door 108, enters downward through a small hole in processing unit and depresses the actuating button on a limit switch 123 inside the housing of the processing unit 2. This energizes a solenoid 120 which causes the pin 129 to retract, thereby unlocking the door 110 on the top of the processing unit 2. As shown in FIGS. 13 and 14, the collection unit 1 is then pushed laterally forward by the user against the exposed end of the processing unit door 110. This door 110 slides laterally to the right into the processing unit as the collection unit advances. Since the collection unit door 108 is restrained by the engagement pins 127, an opening is created between the collection unit and the processing unit 2 as the collection unit is pushed forward into the processing unit. The syringes stored in the collection unit fall through this opening and into the in-feed chute 114 for the grinder 21 located within the processing unit 2. During this operation, any transverse motion of the collection unit with respect to the processing unit is constrained by the vertical side walls of the processing unit's interlock mechanism as shown in FIGS. 2, 3, and 12.

When the collection unit 1 is fully inserted into the processing unit 2, the distal end of the processing unit door 110 makes contact with a second limit switch 112. This switch interrupts power to the solenoid 120, causing the spring-loaded locking pin 129 to be pressed against the side of the processing unit's door slide assembly 113. The collection unit can then be withdrawn from the processing unit by lifting it vertically upward off the processing unit. Two constant-force spring assemblies 124 exert a longitudinal force to the processing unit door 110 to drive it to a closed and locked position. When this door 110 is fully closed, the spring-loaded locking pin 129 drops into the shallow recess of the door slide assembly 113 and prevents further movement of the processing unit door. In addition, spring latches in the bottom of the collection unit close and lock the sliding door 108 in the collection unit.

As a safety feature, limit switch 123 remains deactivated until completion of the entire processing cycle. This prevents a collection unit from being inserted into the processing unit due to engagement of the locking pin 129 with the recess in the processing unit door slide assembly 113.

After the contents of the collection unit are emptied into the processing unit, a grinder 21 contained in the processing unit 2 is activated to grind the syringes into particles or small fragments. In one embodiment, a solenoid-activated trap door (not shown) located at the bottom of the in-feed chute retains the syringes in the chute until the grinder is up to full operating speed. The trap door is then opened, allowing the syringes to drop into the grinder.

Most conventional disposable syringes have a metal needle, but the remaining components are usually made of a thermoplastic material, such as polypropylene. In addition, a small amount of other elastomeric material, such as rubber, may be used for the plunger seal. Thus, the ground material produced by the grinder are largely particles of plastic. Only about 5% of these particles are metal fragments or other materials.

These particles are fed from the grinder into a crucible 22. In the preferred embodiment, an electric heating element built into the crucible is then employed to raise the temperature of the crucible and its contents to approximately 450° F. to sterilize the contents of the crucible 22 and melt the plastic particles into a molten mass. The melting point of polypropylene is approximately 340° F. The metal particles in the crucible are suspended and encapsulated in the melted plastic. In the preferred embodiment, this process requires about 20 minutes using a 600 watt heater. Virtually any type of conventional heater could be substituted.

Figure 4:
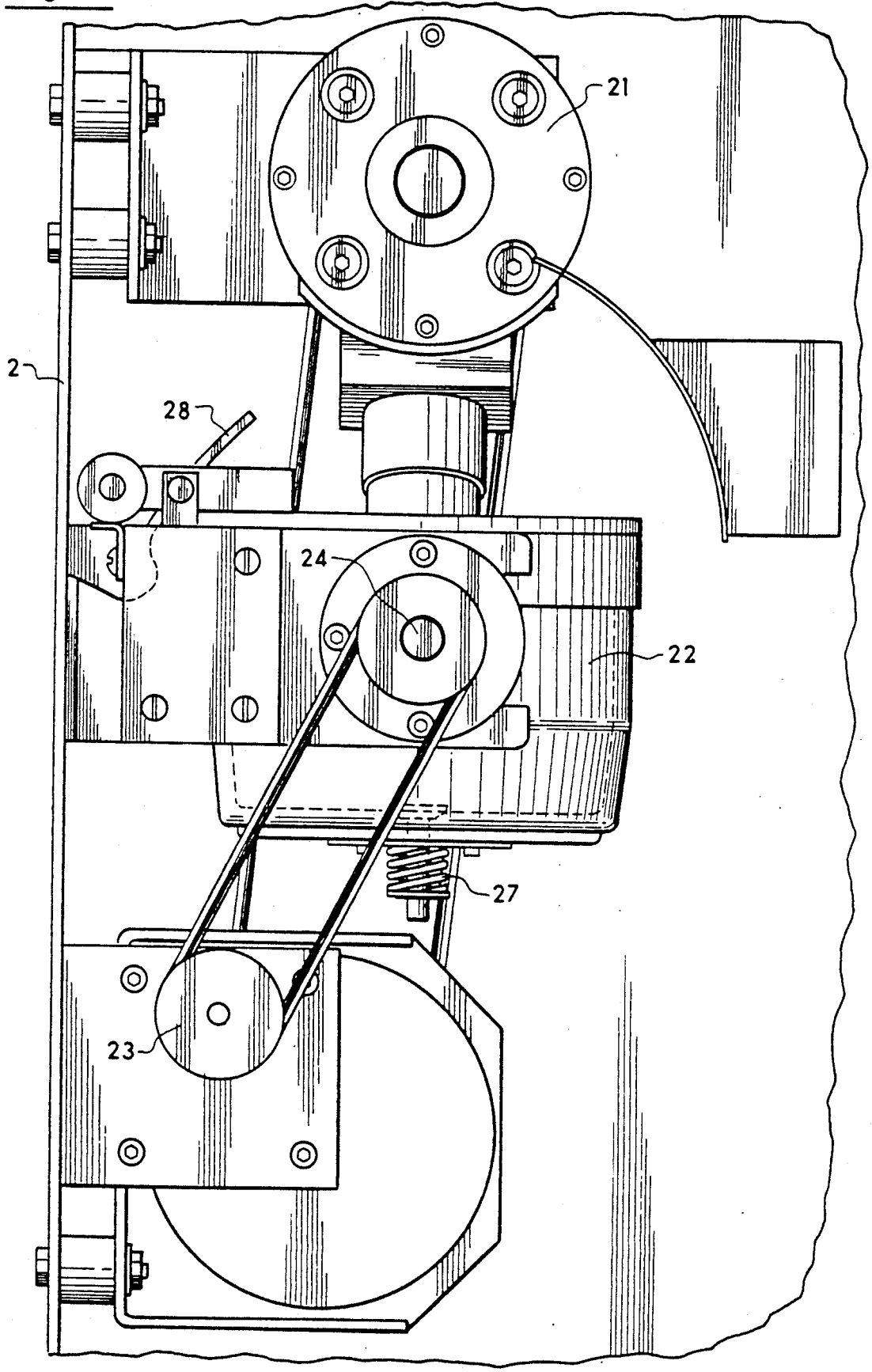
FIG. 4 is a side view showing the crucible assembly in an upright position within the processing unit.
Figure 5:
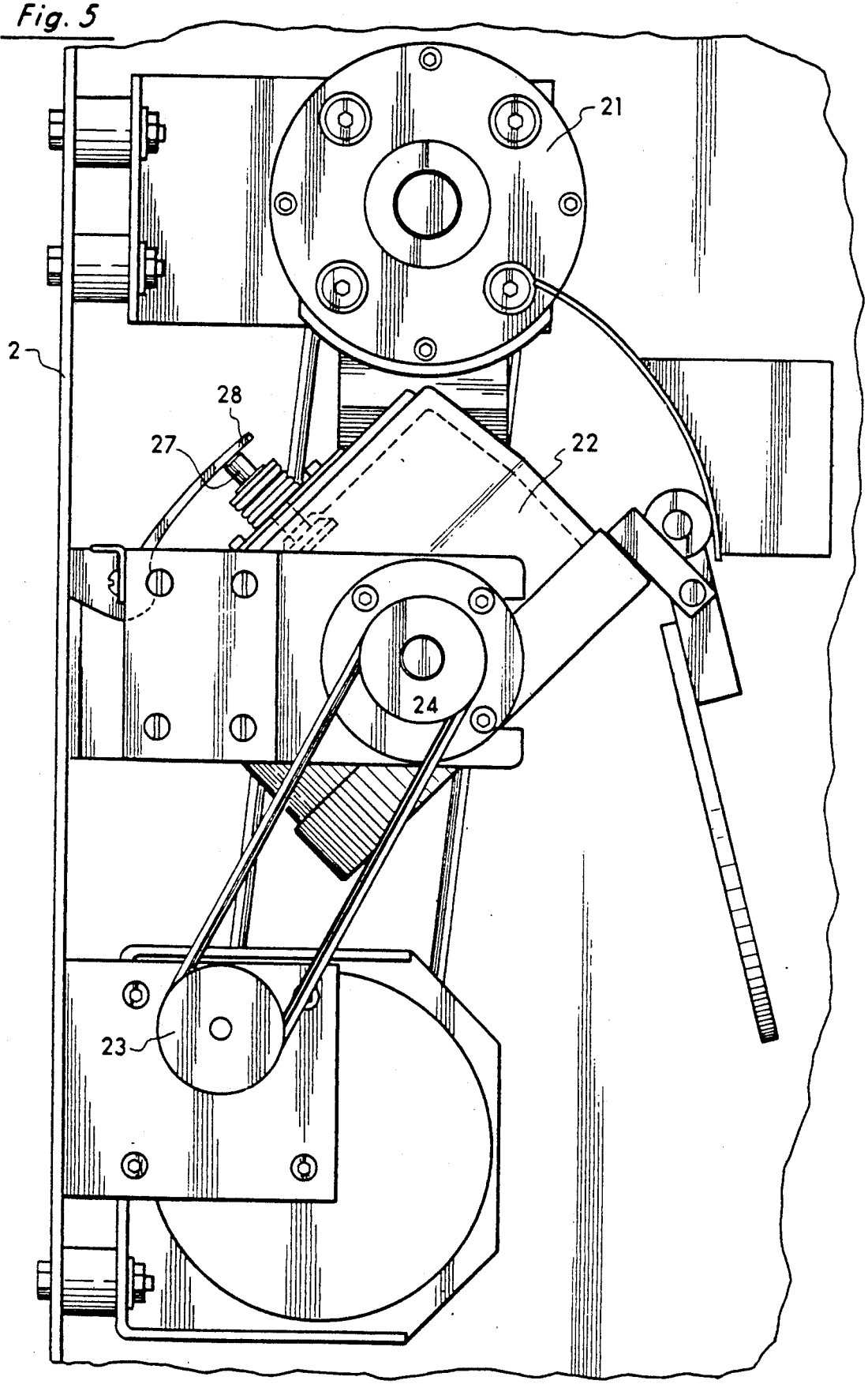
FIG. 5 is a side view showing the crucible assembly in a rotated position within the processing unit.

After the plastic particles have melted, the heater is turned off and the contents of the crucible are allowed to cool to a temperature below the melting point of the plastic to form a solid puck. Surprisingly, experimentation indicates that few, if any, of the metal particles are found at or near the surface of the plastic puck. Thus, the sharp edges of the metal particles are safely encapsulated within the puck. The crucible 22 is pivotably mounted by means of bearings 24 to the housing of the processing unit 2, so that the crucible can be tipped or rotated about a horizontal axis into an inverted position to allow the puck to fall out of the crucible. A motor 23 controls rotation of the crucible 22. FIG. 4 shows the crucible 22 in an upright position. FIG. 5 shows the crucible in its inverted position. To help insure elimination of the puck from the crucible at the end of each operating cycle, a spring-loaded "knock out" pin 27 extends from the interior to the exterior of the crucible through a small hole in the bottom surface of the crucible. The outer end of the pin extends substantially outward beyond the bottom surface of the crucible. A camming surface 28, attached to the housing, contacts the outer end of the pin 27 when the crucible is in an inverted position, thereby moving the pin inward with respect to the crucible, and exerting a positive force on the bottom of the puck to cause it to fall out of the crucible. The puck falls into a tray at the bottom of unit. FIG. 3 shows a tray 26 holding several pucks 30 resulting from the disposal process being removed through an access door 25 in the bottom of the processing unit 2.

The preceding discussion has been primarily limited to disposal of plastic syringes. It should be noted that the present invention is readily adaptable to disposal of types of medical wastes composed primarily of plastics, such as disposable scalpels.

Figure 15:
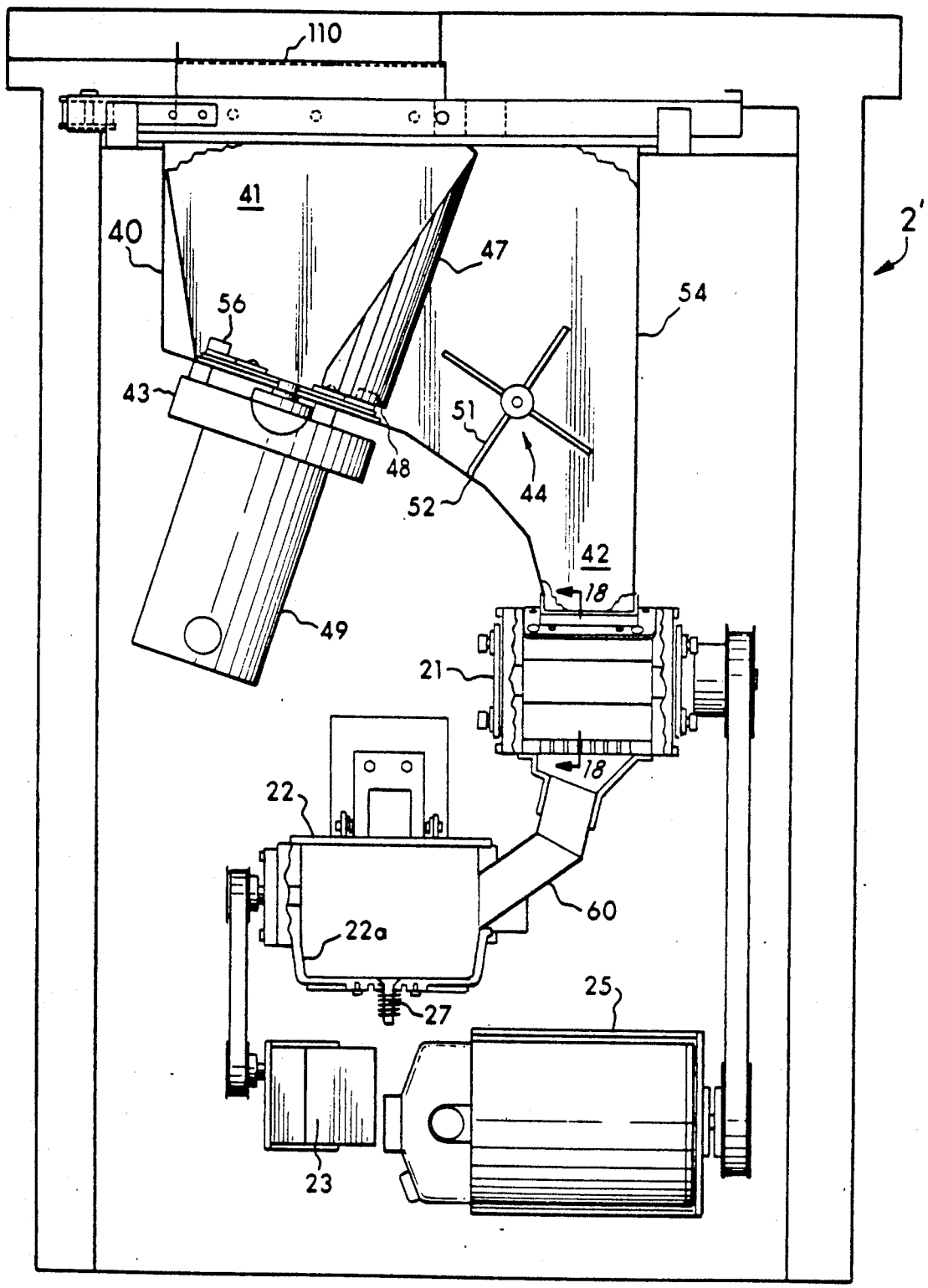
FIG. 15 illustrates a modified processing unit with an enlarged feed hopper.
Figure 16:
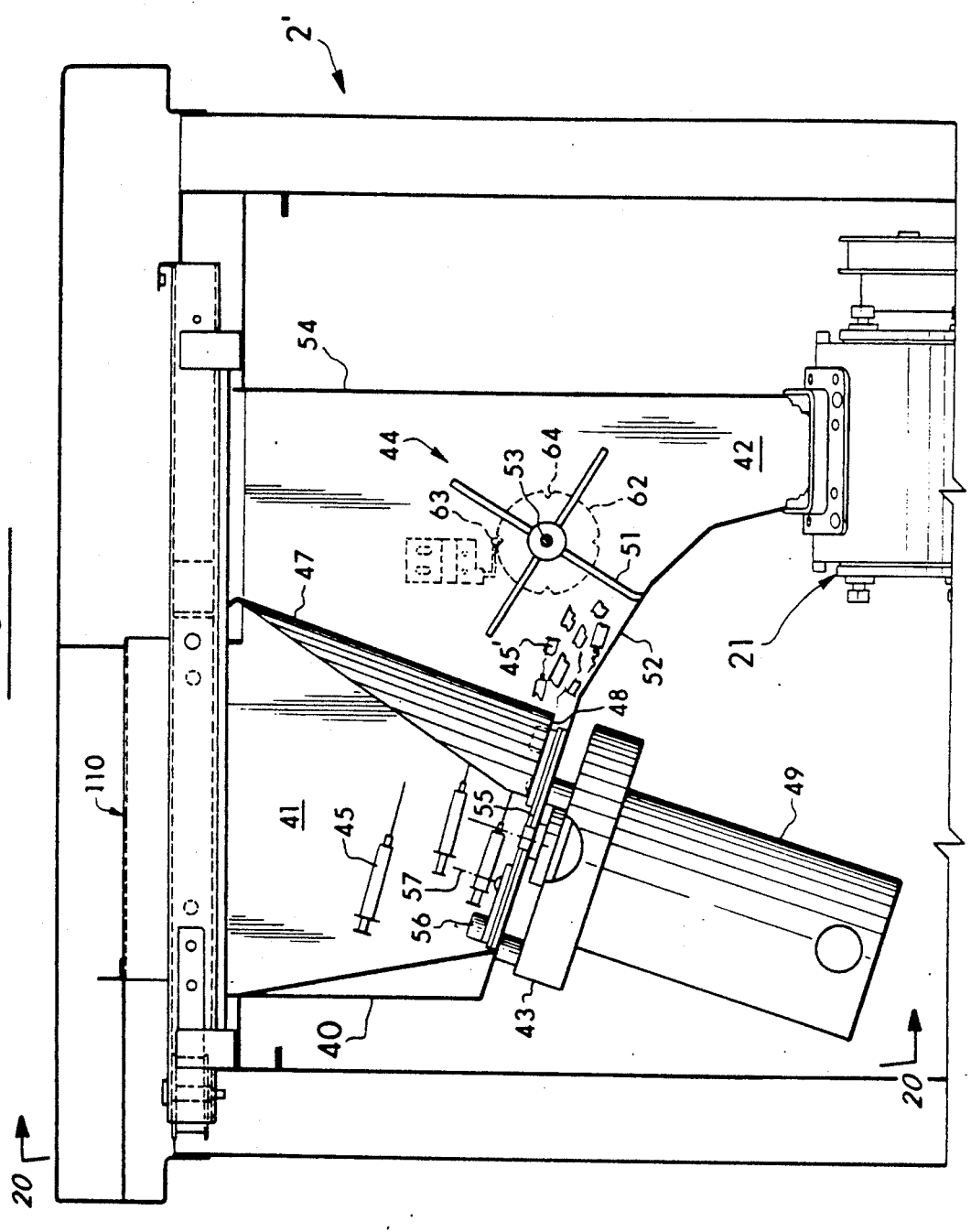
FIG. 16 illustrates further details of the enlarged, modified feed hopper of FIG. 15.

In the embodiment of FIGS. 15-20, the processing unit at 2' is modified to include a larger hopper 40 with an inlet 41 and outlet 42. The modified hopper 40 further includes breaking means 43 and paddle wheel 44. The breaking means 43 (see FIG. 16) serves as a preliminary or first stage grinder to break the incoming syringes 45 into discrete pieces 45' before they are subsequently fed to the grinder 21 to be ground into much smaller particles of plastic and metal. In doing so as shown in FIG. 16, the whole syringes 45 are maintained by the partition 47 in the hopper area just above the breaking means 43 until they are broken into pieces 45' that can then easily pass through the opening or gap 48 in the lower portion of screening partition 47. Thereafter, the broken syringe pieces 45' pass downstream to the paddle wheel 44 and on to the grinder 21.

Figure 17:
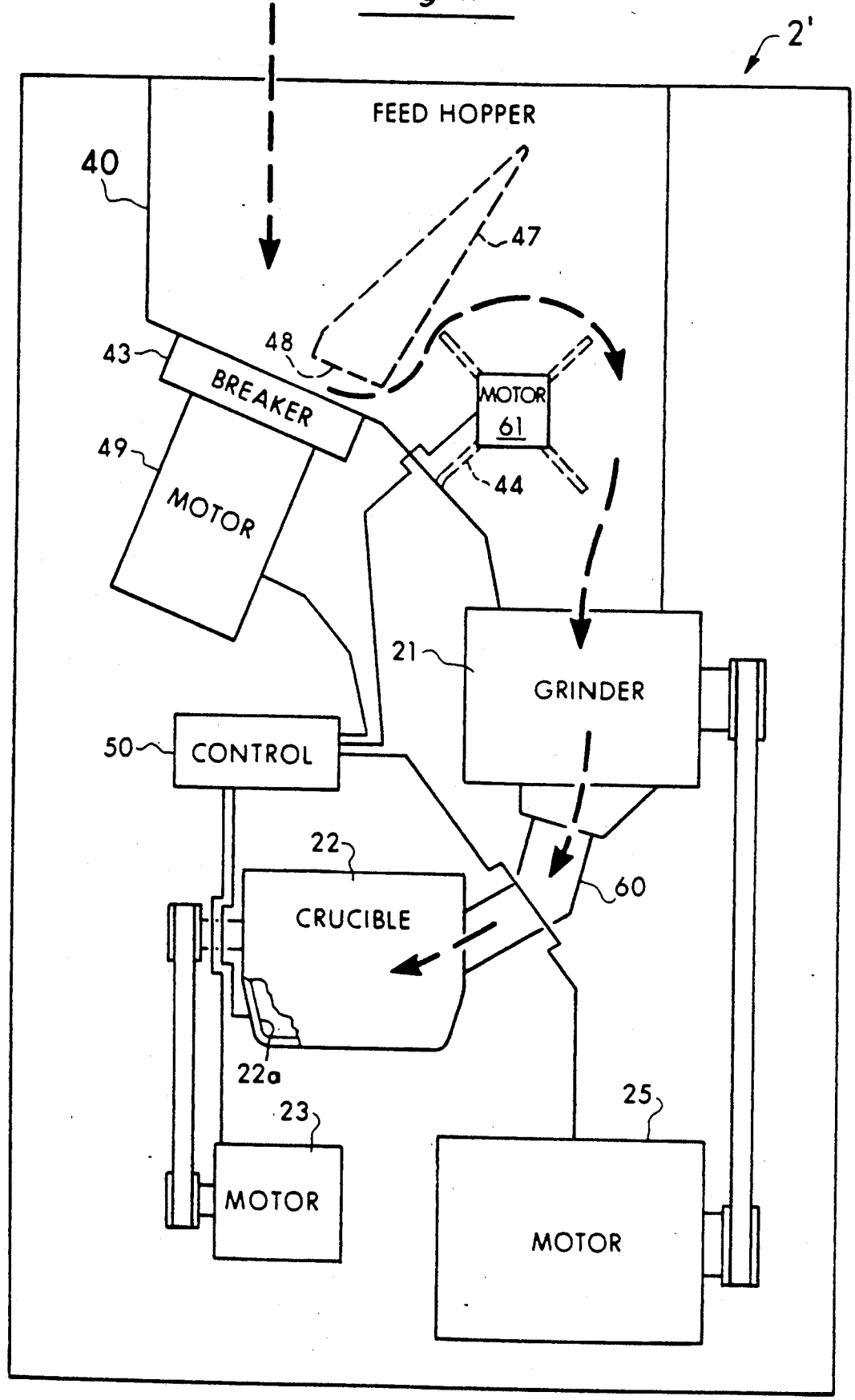
FIG. 17 is a schematic drawing of the modified processing unit.
Figure 18:
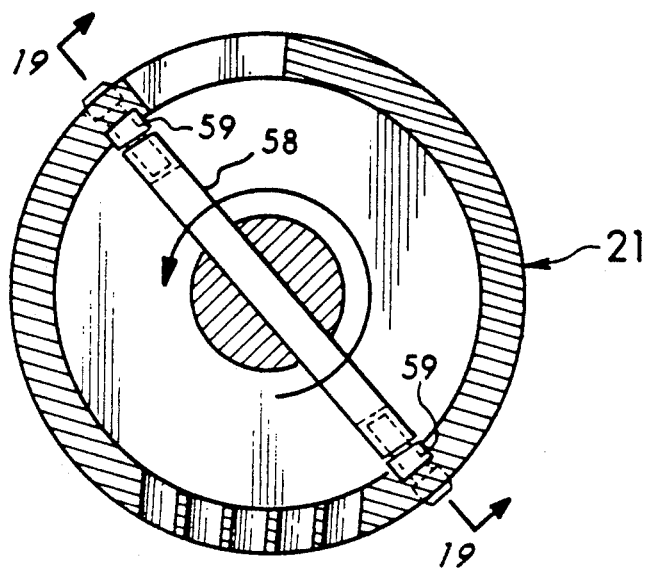
FIG. 18 is a cross-sectional view of the grinder taken along line 18—18 of FIG. 15.
Figure 19:
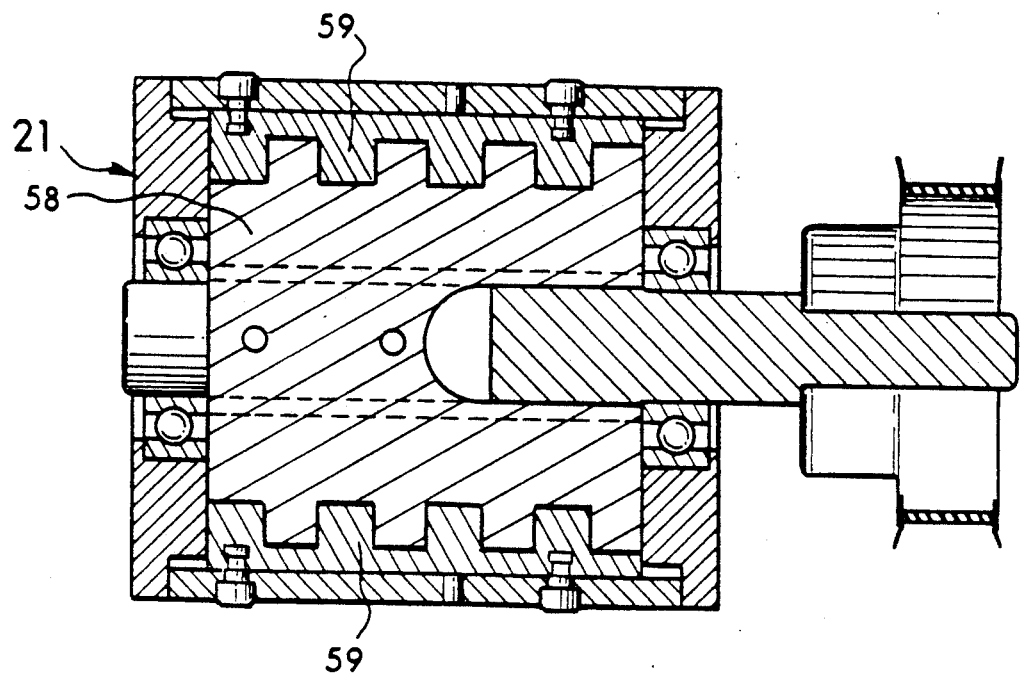
FIG. 19 is a cross-sectional view taken along line 19—19 of FIG. 18.

The paddle wheel 44 of FIGS. 15-17 performs multiple functions including regulating or valving the flow of syringes through the hopper outlet 42. In doing so, it can be operated to selectively allow and prevent the broken syringes 45' from passing out of the hopper outlet 42 to the grinder 21. In the preferred mode of operation, the whole syringes 45 are fed through the hopper inlet 41 onto the breaking means 43 after which the breaker motor 49 is activated by the control or controlling means 50 (see FIG. 17). At this point as best seen in FIG. 16, the paddle wheel 44 is in a stationary position with one of its paddles 51 substantially touching and perpendicular to the lower, inclined hopper wall 52. In this position, the stationary paddle wheel 44 extends substantially across the outlet 42 of the hopper 40 to prevent any of the broken syringes 45' from passing out of the hopper outlet 42 to the grinder 21. As shown in FIG. 16, the axis 53 of the paddle wheel 44 is spaced such that the distance between the axis 53 and the inclined hopper wall 52 is approximately the same and preferably slightly less than the radial extent of the planar paddles 51. In this manner, the lower left rubber paddle 51 in the position of FIGS. 15 and 16 will flex slightly against the hopper wall 52 and form an effective, positive barrier to the passage of the broken syringes 45' along the hopper wall 52. The axis 53 of the paddle wheel 44 is also positioned slightly farther from the second hopper wall 54 than from the wall 52 with the wall 54 as shown in FIGS. 15-17 being spaced farther from the axis 53 than the paddles 51. In this regard and in the operating mode of FIG. 17 with the paddle wheel 44 being rotated clockwise, the broken syringe pieces 45' (and even the odd whole syringe 45 that may pass through the partition gap 48) can easily pass between the paddle wheel 44 and hopper wall 54 through the hopper outlet 42 into the grinder 21. Also, the clockwise rotation and paddles 51 serve to meter the feed to the grinder 21 into discrete batches for more efficient operation.

As stated above, the preferred mode of operation of the breaking means 43 and paddle wheel 44 is to initially operate the breaking means 43 (as well as the grinder 21) for a predetermined amount of time while the paddle wheel 44 remains in its stationary position of FIG. 16. This coordinated operation and delay in the activation of paddle wheel 44 is controlled by the controlling means 50 illustrated in FIG. 17. The delay in initiating the operation of the paddle wheel 44 serves the primary purpose of allowing grinder 21 to come up to speed before syringes (whole or in the broken pieces) are fed to the grinder 21. As shown in FIG. 17, the preferred direction of operation of the paddle wheel 44 is clockwise so that the paddles 51 pass by and wipe the inclined hopper wall 52 in a direction away from the hopper outlet 42 and pass by the second hopper wall 54 in a direction toward the hopper outlet 42. The breaking means 43 is preferably a hammer mill with its rotor 55 mounted adjacent the hopper inlet 41 upstream of the paddle wheel 44 and partition 47. The hammers 56 are then pivotally mounted on the rotor 55 about axes 57 (see FIG. 16) and the motor 49 for the breaking means 43 is controlled by the controlling means 50. The grinder 21 is preferably a fixed shearing device with its sawtooth rotor 58 (see FIGS. 18 and 19) operating against the fixed, sawtooth shear plates 59. With the hammer mill, there is less of a tendency for the breaking means 43 to be jammed. Also, the breaking or pre-grinding of the breaking means 43 enables the grinder 21 to more efficiently grind the syringes into plastic and metal particles that are significantly smaller than the broken syringe pieces 45' being fed to the grinder 21.

The controlling means 50 of the modified processing unit 2' of FIG. 17 also has the added feature that it can efficiently coordinate the operation of the members of the processing unit 2'. In particular, it can control the operation of the grinder motor 25 and grinder 21 with different stages of the disposal cycle to create vibrations in the chute 60 to the crucible 22 and in the crucible 22 itself when it is in its inverted, discharged position of FIG. 5. That is, the controlling means 50 is programmed to control the breaker motor 49, paddle wheel motor 61, grinder motor 25, electric heating means 22a within the walls of the electric crucible 22, and discharge motor 23 which inverts the crucible 22. In the preferred cycle, the whole syringes 45 are fed to the area of the breaking means 43 after which the controlling means 50 starts up the breaker motor 49 and grinder motor 25 with the paddle wheel 44 remaining in the stationary position of FIG. 15. At a predetermined time thereafter, the controlling means 50 operates the paddle wheel motor 61 to drive the paddle wheel 44 and to feed the broken syringe pieces 45' into the grinder 21. The pieces 45' are then ground into plastic and metal particles and delivered through the chute 60 to the crucible 22. With the grinder motor 25 thereafter deactivated, the heating means 22a in the crucible 22 is then activated to heat the crucible 22 and the plastic and metal particles therein to a temperature above the melting point of the plastic particles. After the melting point is reached, the grinder motor 25 is again activated by the controlling means 50. This causes any particles remaining in the chute 60 (e.g., by a prior static electricity charge) to be delivered to the crucible 22 while the temperature of the crucible 22 and its contents is above the melting point of the plastic particles. In the preferred embodiment and for simplicity, the grinder motor 25 is activated substantially at the same time that the heating means 22a is deactivated. The contents of crucible 22 are then allowed to cool to a temperature below the melting point of the plastic particles to produce a solid puck with the metal particles from the ground needles suspended and encapsulated in the plastic. Thereafter, the crucible motor 23 is activated to rotate the crucible 22 about its horizontal axis to its inverted, discharge position of FIG. 5 with the crucible plunger 27 extended. The controlling means 50 then again activates the grinder motor 25 to create vibrations in the inverted crucible 22 to assist the discharge of the puck therefrom.

Figure 20:
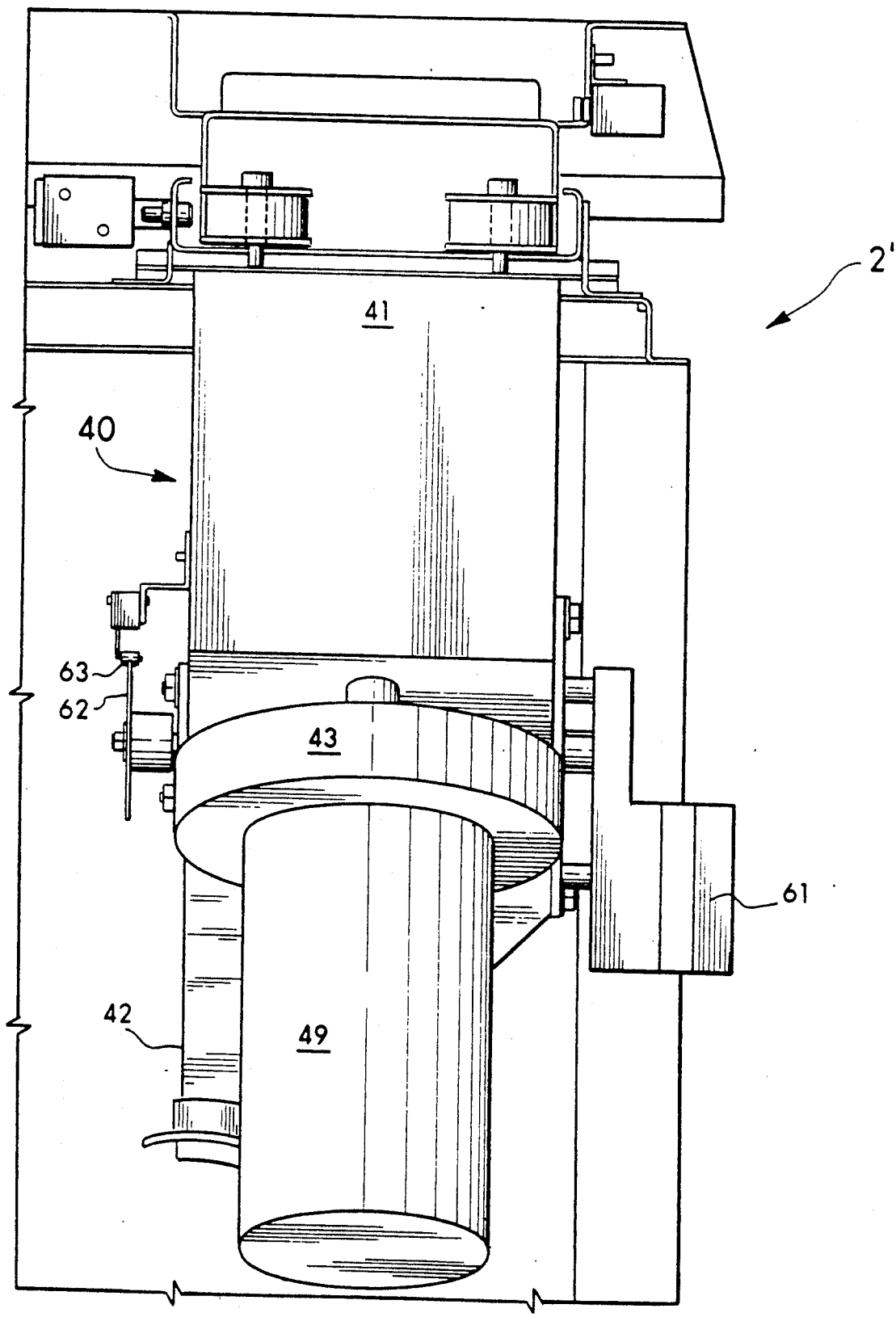
FIG. 20 is a view of the modified feed hopper taken along line 20—20 of FIG. 16.

In the preferred embodiment and during each of the above-mentioned vibrating steps, the controlling means 50 maintains the paddle wheel motor 61 deactivated. In doing so, the paddle wheel 44 is preferably in its stationary position of FIGS. 15 and 16 to prevent the passage of any broken syringe pieces 45' that may have remained in the hopper 40 from entering the grinder 21. To accomplish this, the controlling means 50 also includes the rotating cam 62 and follower switch 63 of FIGS. 16 and 20. More specifically, the controlling means 50 (after the grinder 21 has ground the broken syringe pieces 45' into particles that have been discharged through this chute 60 to the crucible 22) will deactivate both the grinder motor 25 and the paddle wheel motor 61. Since the paddle wheel 44 is operated at significantly lower revolutions per minute (e.g., 4 rpm) than the grinder (e.g., 7,000 rpm) and has significantly less momentum, the paddle wheel 44 will coast to a stop almost immediately and well before the rotor 58 of the grinder 21. However, to insure that the paddle wheel 44 stops in the position of FIGS. 15 and 16 with one of its paddles 51 perpendicular to the hopper wall 52, the cam 62 and switch 63 arrangement of FIGS. 16 and 20 is provided as part of the controlling means 50. In operation, the switch 63 follows the cam 62 which is mounted outside of the hopper 40 for rotation with the paddle wheel 44. When the controlling means 50 sends a message to the grinder motor 25 and paddle wheel motor 61 to disengage, the disengagement command to the paddle wheel motor 61 is delayed until the switch 63 encounters one of the detents 64 in the rotating cam 62 (see FIG. 16). Upon such engagement, the deactivation command is then delivered to the paddle wheel motor 61. The motor 61 thereafter stops the rotation of the paddle wheel 44 almost immediately or after a predetermined coast (e.g., ¼ revolution) in the position of FIGS. 15 and 16 with one of the paddles 51 perpendicular to the inclined hopper wall 52.

While several embodiments of the invention have been shown and described in detail, it is understood that various modifications and changes could be made to them without departing from the scope of the invention.

We claim:

1. An apparatus for disposal of used syringes made primarily of plastic components and a metal needle, said apparatus including:
   means for grinding said syringes into particles of plastic and metal,
   a crucible for receiving said particles produced by said grinding means, said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein,
   means for rotating said crucible about a horizontal axis into a substantially inverted position, and
   means for vibrating said crucible while in said inverted position to assist discharge of said puck out of said crucible.

2. The apparatus of claim 1 wherein said vibrating means includes a motor and means to selectively activate said motor when said crucible is in said inverted position to create vibrations in said crucible to assist discharge of said puck therefrom.

3. An apparatus for disposal of used syringes made primarily of plastic components and a metal needle, said apparatus including:
  means for grinding said syringes into particles of plastic and metal;
  a crucible for receiving said particles produced by said grinding means, said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein, said grinding means including a grinder and motor for driving said grinder wherein operation of said motor to drive said grinder vibrates said crucible,
  means for rotating said crucible about a horizontal axis into a substantially inverted position, and
  means for vibrating said crucible while in said inverted position to assist discharge of said puck out of said crucible wherein said means for vibrating said crucible includes means to selectively activate said motor to drive said grinder when said crucible is in said inverted position to create vibrations in said crucible.

4. The apparatus of claim 3 further including means for feeding said syringes into said grinder and means for preventing said feeding during operation of said motor and grinder to vibrate said crucible when said crucible is in said inverted, discharge position.

5. A method for disposal of used syringes made primarily of plastic components and a metal needle, said method including the steps of:
  (a) grinding said syringes into particles of plastic and metal,
  (b) heating said particles in a crucible to a temperature above the melting point of said plastic particles,
  (c) cooling the contents of said crucible to produce a solid puck of plastic with the metal particles suspended and encapsulated therein,
  (d) rotating said crucible about a horizontal axis into a substantially inverted position, and
  (e) vibrating said crucible while in said inverted position to assist discharge of the puck out of the crucible.

6. A method for disposal of used syringes made primarily of plastic components and a metal needle, said method including the steps of providing a grinder, motor for driving said grinder, and crucible wherein operation of said motor to drive the grinder vibrates the crucible and further including the steps of:
  (a) grinding said syringes into particles of plastic and metal,
  (b) heating said particles in said crucible to a temperature above the melting point of said plastic particles,
  (c) cooling the contents of said crucible to produce a solid puck of plastic with the metal particles suspended and encapsulated therein,
  (d) rotating said crucible about a horizontal axis into a substantially inverted position, and
  (e) vibrating said crucible while in said inverted position to assist discharge of the puck out of the crucible by operating said motor to drive said grinder when said crucible is in said inverted position to create vibrations in said crucible.

7. The method of claim 6 wherein step (a) includes the further limitation of feeding syringes to said grinder and step (e) includes the further limitation of preventing said feeding during operation of said motor and grinder to vibrate said crucible when said crucible is in said inverted, discharge position.

8. An apparatus for disposal of used syringes made primarily of plastic components and a metal needle, said apparatus including:
  means for grinding said syringes into particles of plastic and metal, a crucible for receiving said particles produced by said grinding means, and a chute extending between said grinding means and said crucible for delivering said particles to said crucible,
  said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein, and
  means for vibrating said chute while the temperature of said crucible and its contents is above the melting point of said plastic particles wherein any particles remaining in said chute will be delivered to said crucible while the temperature of the crucible and its contents is above said melting point.

9. The apparatus of claim 8 wherein said vibrating means vibrates said chute substantially at the same time said controlling means deactivates said heating means.

10. The apparatus of claim 8 wherein said vibrating means includes a motor and means to selectively activate said motor while the temperature of said crucible and its contents is above the melting point of said plastic particles.

11. An apparatus for disposal of used syringes made primarily of plastic components and a metal needle, said apparatus including:
  means for grinding said syringes into particles of plastic and metal, a crucible for receiving said particles produced by said grinding means, and a chute extending between said grinding means and said crucible for delivering said particles to said crucible, said grinding means including a grinder and motor for driving said grinder wherein operation of said motor to drive said grinder vibrates said chute,
  said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein, and
  means for vibrating said chute while the temperature of said crucible and its contents is above the melting point of said plastic particles wherein any particles remaining in said chute will be delivered to said crucible while the temperature of the crucible and its contents is above said melting point, said means for vibrating said chute including means to selectively activate said motor to drive said grinder while the temperature of the crucible and its contents are above said melting point to create vibrations in said chute.

12. The apparatus of claim 11 wherein said vibrating means vibrates said chute substantially at the same time said controlling means deactivates said heating means.

13. The apparatus of claim 11 further including means for feeding said syringes into said grinder and means for preventing said feeding during operation of said motor and grinder to vibrate said chute while the temperature of the crucible and its contents is above said melting point.

14. A method for disposal of used syringes made primarily of plastic components and a metal needle, said method including the steps of:
  (a) grinding said syringes into particles of plastic and metal,
  (b) delivering the particles of step (a) through a chute to a crucible,
  (c) heating said particles in said crucible to a temperature above the melting point of said plastic particles,
  (d) vibrating said chute while the temperature of said crucible and its contents is above said melting point to deliver any particles remaining in said chute to said crucible,
  (e) cooling the contents of said crucible to produce a solid puck of plastic with the metal particles suspended and encapsulated therein, and
  (f) discharging said puck from said crucible.

15. A method for disposal of used syringes made primarily of plastic components and a metal needle, said method including the steps of providing a grinder, motor for driving said grinder, and chute wherein operation of said motor to drive the grinder vibrates the chute and further including the steps of:
  (a) grinding said syringes into particles of plastic and metal;
  (b) delivering the particles of step (a) through a chute to a crucible,
  (c) heating said particles in said crucible to a temperature above the melting point of said plastic particles,
  (d) vibrating said chute by operating said motor to drive said grinder while the temperature of said crucible and its contents is above the melting point of said plastic particles,
  (e) cooling the contents of said crucible to produce a solid puck of plastic with the metal particles suspended and encapsulated therein, and
  (f) discharging said puck from said crucible.

16. The method of claim 15 wherein step (a) includes the further limitation of feeding syringes to said grinder and step (d) includes the further limitation of preventing said feeding during operation of said motor and grinder to vibrate said chute while the temperature of the crucible and its contents is above said melting point.

17. An apparatus for disposal of used syringes made primarily of plastic components and a metal needle, said apparatus including:
  means for grinding said syringes into particles of plastic and metal, and
  means for feeding said syringes to said grinding means, said feeding means including a hopper with an inlet and outlet and regulating means to selectively allow and substantially prevent passage of syringes through said hopper outlet to said grinding means, said regulating means being positionable in a first, stationary position,
  said regulating means including a paddle wheel, means to mount said paddle wheel adjacent the outlet of said hopper for rotation about an axis, and means to rotate said paddle wheel about said axis, said paddle wheel having a plurality of paddles spaced about and extending outwardly of said axis for a first distance, said hopper further including a first wall adjacent said hopper outlet, said first wall being spaced slightly less than said first distance from said paddle wheel axis and being fixed in a predetermined position relative to said paddle wheel axis, said paddles being flexible wherein said paddle wheel in said first, stationary position has one of said flexible paddles extending outwardly of said axis to touch and flex against said first hopper wall to positively prevent the passage of syringes to said hopper outlet between said paddle wheel axis and said first hopper wall, and said hopper further includes a second hopper wall adjacent said hopper outlet, said second wall being spaced slightly more than said first distance from said paddle wheel axis wherein said broken syringes can pass to said hopper outlet between said paddles of said paddle wheel and said second hopper wall.

18. The apparatus of claim 17 wherein said first hopper wall is inclined to the horizontal, said paddles are substantially planar, and said one paddle in said first position is substantially perpendicular to said first hopper wall.

19. The apparatus of claim 17 wherein said means to rotate said paddle wheel rotates said paddle wheel about said axis with said paddles moving by said first wall in a direction away from said outlet and moving by said second wall in a direction toward said outlet wherein said paddle wheel feeds said syringes to said grinder by said second wall.

20. An apparatus for disposal of used syringes made primarily of plastic components and a metal needle, said apparatus including:
  means for grinding said syringes into particles of plastic and metal,
  a crucible for receiving said particles produced by said grinding means, said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein,
  means for rotating said crucible about a horizontal axis into a substantially inverted position, and
  means for vibrating said crucible while in said inverted position to assist discharge of said puck out of said crucible, said vibrating means including said grinding means wherein operation of said grinding means vibrates said crucible, said vibrating means further including means for selectively operating said grinding means to deactivate said grinding means during at least a portion of the time said heating means is heating said crucible and the particles therein and to thereafter activate said grinding means while the crucible is in said inverted position to create vibrations in said crucible to assist discharge of the puck therefrom.

21. The apparatus of claim 20 further including means for feeding said syringe into said grinding means and means for preventing said feeding during operation of grinding means to vibrate said crucible when said crucible is in said inverted, discharge position.

22. An apparatus for disposal of used syringes made primarily of plastic components and a metal needle, said apparatus including:

means for grinding said syringes into particles of plastic and metal, a crucible for receiving said particles produced by said grinding means, and a chute extending between said grinding means and said crucible for delivering said particles to said crucible, said crucible having heating means and means for controlling said heating means, said controlling means selectively activating said heating means to heat said crucible and the particles therein to a temperature above the melting point of said plastic particles and thereafter deactivating said heating means to allow said crucible and the contents therein to cool to a temperature below said melting point to produce a solid puck of plastic with said metal particles suspended and encapsulated therein, and means for vibrating said chute and means for selectively operating said vibrating means to deactivate said vibrating means during at least a portion of the time said heating means is heating said crucible and the particles therein and to thereafter activate said vibrating means while the temperature of said crucible and its contents is above the melting point of said plastic particles wherein any particles remaining in said chute will be delivered to said crucible while the temperature of the crucible and its contents is above said melting point.

23. The apparatus of claim 22 further including means for feeding said syringes into said grinding means and means for preventing said feeding during operation of said grinding means to vibrate said chute while the temperature of the crucible and its contents is above said melting point.

24. The apparatus of claim 22 wherein said vibrating means vibrates said chute substantially at the same time said controlling means deactivates said heating means.

* * * * *